United States Patent [19]

Harris et al.

[11] Patent Number: 4,587,050

[45] Date of Patent: May 6, 1986

[54] SUBSTITUTED ENANTHOLACTAM DERIVATIVES AS ANTIHYPERTENSIVES

[75] Inventors: Elbert E. Harris, Westfield; Eugene D. Thorsett, Fanwood; Arthur A. Patchett, Westfield, all of N.J.

[73] Assignee: Merck & Co., Inc., Rahway, N.J.

[21] Appl. No.: 700,223

[22] Filed: Feb. 11, 1985

Related U.S. Application Data

[63] Continuation-in-part of Ser. No. 394,971, Jul. 2, 1982, abandoned, which is a continuation-in-part of Ser. No. 280,971, Jul. 7, 1981, abandoned, which is a continuation-in-part of Ser. No. 179,141, Aug. 18, 1980, abandoned.

[51] Int. Cl.$^4$ ............................................. C07D 225/02

[52] U.S. Cl. .....................................................260/239.3 R

[58] Field of Search ................................. 260/239.3 R

[56] References Cited

U.S. PATENT DOCUMENTS

| | | | |
|---|---|---|---|
| 4,052,511 | 10/1977 | Cushman et al. | 260/239 A |
| 4,129,571 | 12/1978 | Ondetti et al. | 546/208 |
| 4,154,960 | 5/1979 | Ondetti et al. | 546/208 |

*Primary Examiner*—Robert T. Bond
*Attorney, Agent, or Firm*—Salvatore C. Mitri; Michael C. Sudol

[57] ABSTRACT

The invention in its broad aspects relates to enantholactam derivatives which are useful as angiotensin converting enzyme inhibitors and antihypertensives.

13 Claims, No Drawings

SUBSTITUTED ENANTHOLACTAM DERIVATIVES AS ANTIHYPERTENSIVES

BACKGROUND OF INVENTION

This application is a continuation-in-part of pending application Ser. No. 394,971 filed July 2, 1982 now abandoned, which in turn, is a continuation-in-part of prior application Ser. No. 280,971 filed July 7, 1981 now abandoned which, in turn, is a continuation-in-part of prior application Ser. No. 179,141 filed August 18, 1980, now abandoned.

The invention in its broad aspects related to enantholactam derivatives which are useful as angiotensin converting enzyme inhibitors and as antihypertensives. The compounds of this invention can be shown by the following formula:

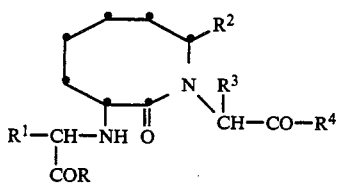

wherein
R and $R^4$ are the same or different and are
hydroxy,
lower alkoxy,
lower alkenoxy,
aryloxy such as phenoxy dilower alkylamino lower alkoxy (e.g., dimethylaminoethoxy), and acylamino substituted lower alkoxy (e.g., acetylaminoethoxy, nicotinoylaminoethoxy, succinimidoethoxy),
acyloxy lower alkoxy (e.g., pivaloyloxyethoxy),
arloweralkoxy, (such as benzyloxy, methoxybenzyloxy),
amino, hydroxyamino;
$R^1$ is hydrogen,
alkyl of from 1 to 12 carbon atoms which include straight and branched alkyl groups;
alkenyl of 2 to 12 carbon atoms;
alkynyl of 2 to 12 carbon atoms;
substituted loweralkyl wherein the substituent(s) can be halo, hydroxy, lower alkoxy, aryloxy (such as phenoxy), amino, lower alkylamino, aminoloweralkylthio, aminoloweralkoxy, di-lower alkylamino, acylamino (such as acetamido and benzamido), arylamino (such as phenylamino), guanidino, phthalimido, mercapto, loweralkylthio, arylthio (such as phenylthio, carboxy, carboxamido or carboloweralkoxy, arloweralkyl, arloweralkenyl, heteroarlower alkyl or heteroarlower alkenyl (such as benzyl, styryl, indolylethyl, imidazolylmethyl, naphthylethyl), substituted arloweralkyl or substituted heteroarloweralkyl, wherein the aryl or heteroaryl substituent(s) is halo, dihalo, lower alkyl, hydroxy, lower alkoxy, amino, aminomethyl, phenyloxy, acylamino, diloweralkylamino, loweralkylamino, carboxyl, haloloweralkyl, acyl, or aroyl; substituted arloweralkyl or substituted heteroarloweralkyl
wherein the alkyl portion can be substituted by amino, hydroxyl or acylamino;

$R^3$ is hydrogen, lower alkyl, phenyl, phenyl lower alkyl, hydroxyphenyl lower alkyl, hydroxy lower alkyl, amino lower alkyl, acylamino lower alkyl, guanidino lower alkyl, imidazolyl lower alkyl, indolyl lower alkyl, mercapto lower alkyl or lower alkyl thio lower alkyl;
$R^2$ is hydrogen, lower alkyl, cycloalkyl, aminoalkyl, hydroxyalkyl, aryl, heteroaryl, aralkyl, heteroaralkyl, heterocycloalkyl, or substituted aryl wherein the substituent is halo, alkyl, aminoalkyl, or alkoxy;
and, the pharmaceutically acceptable salts thereof.

As used throughout this application, including the claims, and unless specified otherwise:
alkyl denotes straight and branched hydrocarbons of $C_2$-$C_{12}$ and loweralkyl denotes straight and branched hydrocarbons of $C_1$-$C_8$;
alkenyl denotes straight and branched hydrocarbons of $C_2$-$C_{12}$ and loweralkenyl denotes straight and branched hydrocarbons of $C_2$-$C_8$, each of which contain a double bond;
alkynyl denotes straight and branched hydrocarbons of $C_2$-$C_{12}$ and loweralkynyl denotes straight and branched hydrocarbons of $C_2$-$C_8$, each of which contain a triple bond;
aryl and the prefix "ar" denote unsubstituted aromatic ring or rings of $C_6$-$C_{12}$ such as, for example, phenyl, naphthyl, biphenyl;
acyl denotes a carboxylic acid derivative represented by the formula

wherein R is alkane, aralkane, arene, heteroarene, heteroaralkene, and substituted derivatives thereof so that acyl denotes, for example, alkanoyl, aroyl, aralkanoyl, heteroaryl, heteroaralkanoyl, and the like;
cycloalkyl denotes an unsubstituted alkyl ring of $C_3$-$C_{10}$;
hetero denotes the heteroatoms N, O or S;
heteroaryl denotes an aryl group containing a heteroatom;
heteroacycle denotes a saturated or unsaturated aromatic or non-aromatic cyclic compound containing a heteroatom; and,
halogen and halo denote F, Br, Cl or I atoms.

Exemplary loweralkyl or lower alkenyl groups for example, methyl, ethyl, propyl, isopropyl, butyl, isobutyl, t-butyl, pentyl, isopentyl, hexyl or vinyl, allyl, butenyl, and the like, and exemplary aralkyl groups include, for example, benzyl, methoxybenzyl and the like. Illustrative heteroaryl groups include, for example, pyridyl, thienyl, furyl, indolyl, benzthienyl, imidazoyl, thiazolyl and quinolinyl.

Preferred are those compounds of Formula I wherein:
R and $R^4$ are independently hydroxy, lower alkoxy or arloweralkoxy;
$R^1$ is alkyl having from 1 to 8 carbon atoms, substituted lower alkyl wherein the alkyl group has 1-5 carbon atoms and the substituent is amino, acylamino, hydroxy, aminoloweralkylthio, aminoloweralkoxy, arylthio, aryloxy or arylamino, aralkyl or heteroaralkyl wherein the alkyl portion has 1 to 3 carbon atoms (such as phenethyl or indolylethyl) or substituted arloweralkyl (phenyl lower alkyl or naphthyl lower alkyl) and substituted heteroarloweralkyl wherein the alkyl groups have 1-3 carbons optionally substituted with amino, hydroxy or acylamino and wherein the substituent(s) on the aryl or heteroaryl groups is halo, dihalo, amino, aminoalkyl, hydroxy, lower alkoxy, lower alkyl, phenoxy or benzoyl;

$R^2$ is hydrogen, lower alkyl, aminoloweralkyl, aryl, aralkyl, heteroaryl, or heteroaralkyl;

$R^3$ is hydrogen, lower alkyl, phenyl lower alkyl, hydroxy phenyl lower alkyl, amino lower alkyl, imidazolyl lower alkyl, indolyl lower alkyl, lower alkyl thio loweralkyl.

More preferred are compounds of Formula I wherein:

R and $R^4$ are independently hydroxy, lower alkoxy, or arlowralkoxy;

$R^3$ is hydrogen, lower alkyl, amino lower alkyl, indolyl lower alkyl, phenyl lower alkyl;

$R^2$ is hydrogen or lower alkyl;

$R^1$ is alkyl from 1 to 8 carbon atoms; substituted lower alkyl wherein the alkyl group has 1-5 carbon atoms and the substituent is amino, acylamino, hydroxy, aminoloweralkylthio, arylthio aryloxy; aralkyl heteroaralkyl wherein the alkyl portion has 1-3 carbon atoms (such as phenethyl or indolylethyl) or substituted arlowralkyl and substituted heteroarloweralkyl wherein the alkyl groups have 1-3 carbons optionally substituted with amino, hydroxy or acylamino and wherein the substitutent(s) on the aryl or heteroaryl groups is halo, amino, aminoalkyl, hydroxy, or lower alkoxy.

Most preferred are compounds of Formula I wherein $R^3$ is hydrogen or lower akyl;

$R^1$ is alkyl of 1-8 carbons; substituted lower alkyl wherein the alkyl group has 1-5 carbon atoms and the substituent is amino, acylamino, hydroxy, arylthio, aryloxy; aralkyl or heteroaralkyl wherein the alkyl portion has 1-3 carbon atoms (such as phenethyl or indolylethyl); or substituted arloweralkyl or substituted heteroarloweralkyl wherein the alkyl groups have 1-3 carbons and the substituents in the aryl or heteroaryl groups are halo, amino, aminoalkyl, hydroxy, or loweralkoxy; $R^2$ is hydrogen or lower alkyl; R and $R^4$ are independently hydroxy, lower alkoxy or benzyloxy.

The preferred, more preferred and most preferred compounds also include the pharmaceutically acceptable salts thereof.

The products of Formula (I) and the preferred subgroups can be produced by one or more of the methods and subroutes depicted in the following equations. The definitions of R, $R^1$, $R^2$, $R^3$, and $R^4$ are the same as in Formula (I) except where noted.

A

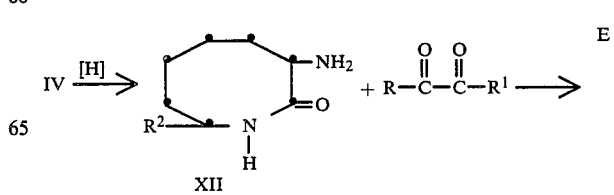

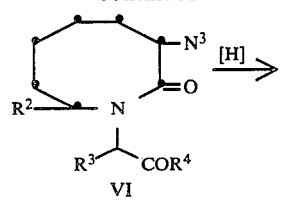

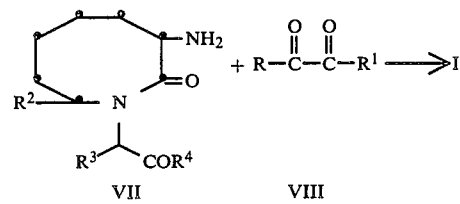

B

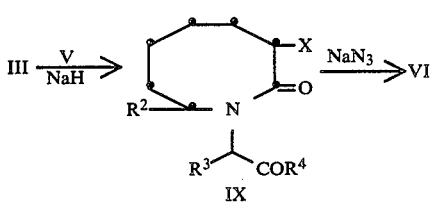

C

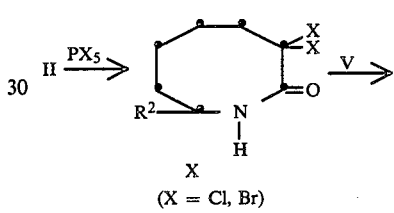

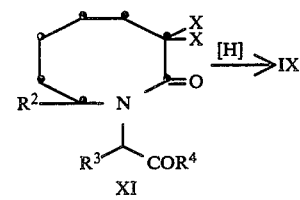

D

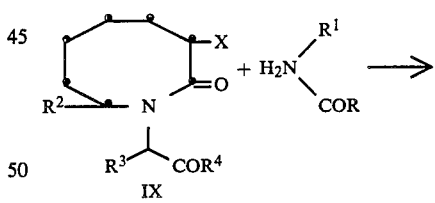

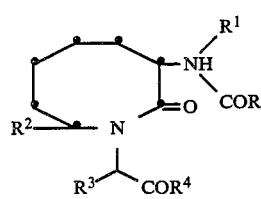

E

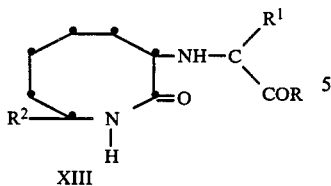

XIII

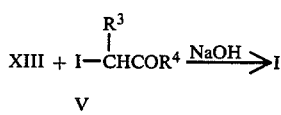

Perhydroazocin-2-one (II) or an 8-substituted derivative prepared from a 2-substituted cycloheptanone by the procedure of Blicke et al., *J. Am. Chem. Soc.*, 76, 2317 (1954) is converted to (III), with PX$_5$, X=Br or Cl [Nagasawa et al., *J. Med. Chem.*, 14, 501 (1971)]. Reaction of III with sodium or lithium azide in a solvent such as DMF or ethanol [see, for example, Brenner et al., *Helv. Chem. Acta*, 41, 181 (1958)] affords (IV) which can be alkylated with an iodoester (V) in the presence of a strong base, like sodium hydride, in a solvent such as DMF or THF to produce (VI). Reduction of (VI) with hydrogen and a suitable catalyst, such as palladium on carbon, affords (VII). Intermediate (VII) is then reductively coupled with a keto acid or ester (VIII) in a solvent such as ethanol using a catalyst such as palladium on carbon to afford (I). Alternatively, sodium cyanoborohydride can be used to effect the reduction.

Groups R and R$_4$ may be modified by known methods, if desired. For example, if R=OEt and R$_4$ =O-t-Bu, the diester (I) can be converted to the monoester R=OEt and R$_4$=OH by treatment with trifluoroacetic acid. If R=R$_4$=OEt, (I) can be converted to the diacid R=R$_4$=OH by basic hydrolysis.

Alternatiely, (III) may be alkylated with (V) in the presence of a strong base, like sodium hydride, and the intermediate (IX) converted to (VI) by reaction with an azide salt as described above.

If desired, (IX) may be prepared by the alkylation of (X) [alternate conditions of Nagasawa, above]with (IV) to afford intermediate (XI). Treatment of (XI) with hydrogen and a catalyst, such as palladium on carbon affords (IX).

Alternatively, IX (X=Cl, Br, R$_4$=OH) may be converted to the iodo compound IX (X=I) by known methods, for example, sodium iodide in acetone. Reaction of this iodo lactam with an amino acid ester in a solvent such as toluene or DMF in the presence of a halide scavenger such as Ag$_2$O gives I (R≠OH, R$_4$≠OH).

If desired, IV may be reduced with hydrogen in the presence of a suitable catalyst to afford XII which can be alkylated with a ketoester in the presence of hydrogen an a suitable catalyst to give XIII. Alternatively, sodium cyanoborohydride may be used. Alkylation of XIII to afford I (R≠OH, R$_4$≠OH) can be carried out with an iodoester in the presence of a strong base such as sodium hydride in a solvent such as THF.

The starting materials which are required for the above processes herein described are known in the literature or can be made by known methods from known starting materials.

In products of general Formula (I), the carbon atoms to which, R$^1$, R$^2$ and R$^3$ are attached and the ring carbon atom to which the fragment

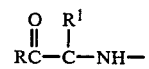

is attached may be asymmetric. Thus, the compounds of this invention exist in diastereoisomeric forms or in mixtures thereof. The above described syntheses can utilize racemates, enantiomers or diastereomers as starting materials. When diastereomeric intermediates or products result from the synthetic procedures, the diastereomeric intermediates or products can be separated by chromatographic or fractional crystallization methods. When racemic mixtures result, they may be resolved by crystallization of salts of optically active acids or bases or by other methods known in the art. These part-structures

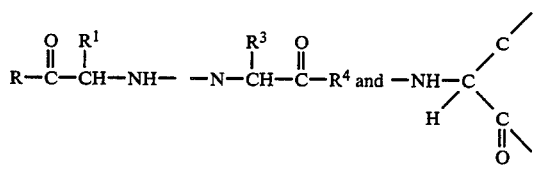

of Formula (I) can be in two configurations (S or R) and both are within the scope of this invention, although S is generally preferred. Both configurations at the carbon to which R$^2$ is attached are encompassed within this invention.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like. Also salts with organic and inorganic acids may be prepared; e.g., HCl, HBr, H$_2$SO$_4$, H$_3$PO$_4$, methanesulfonic, toluensulfonic, maleic, fumaric, camphorsulfonic acids. The non-toxic physiologically acceptable salts are particularly valuable, although other salts are also useful, e.g., in isolating or purifying products.

The salts may be formed by conventional means, as by reacting the free acid or free base forms of the product iwth one or more equivalents of the appropriate base or acid in a solvent or medium in which the salt is insoluble, or in a solvent or medium in which the salt is insoluble, or in a solvent such as water which is then removed in vacuo or by freeze-drying or by exchanging the ions of an existing salt for another ion on a suitable ion exchange resin.

The compounds of this invention inhibit angiotensin converting enzyme and thus block conversion of the decapeptide angiotensin I to angiotensin II. Angiotensin II is a potent presor substance. Thus blood-pressure lowering results from inhibition of its biosynthesis especially in animals and humans whose hypertension is angiotensin II related. Furthermore, convertng enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with reno-vascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys.. Acta*, 206 136 (136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, scleroderma, primary and secondary pulmonary hypertension, renal failure and renal vascular hypertension, and in the management of vascular disorders such as migraine. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 200 mg. per patient per day which can be administered in single or multiple doses. Preferably, the dosage range will be about 2.5 to 100 mg. per patient per day.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl[phenoxy{-2-propanol, polythiazide, the pivalogloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl} benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–100 milligrams per day range can be effectively combined at levels at the 0.5–100 milligrams per day range with the following comounds at the indicated per day dose range: hydrochlorothiazide (10–100 mg), timolol (5–60 mg), methyl dopa (65–2000 mg), the pivaloyloxyethyl ester of methyl dopa (30–1000 mg), indacrinone and variable ratios of its enantiomers (25–150 mg) and (+)-4-{3-{[2-(1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus timolol (5–60 mg) plus converting enzyme inhibitor of this invention (0.5–100 mg) or hydrochlorothiazide (10–100 mg) plus amiloride (5–20 mg) plus converting enzyme inhibitor of this invention (0.5–100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 0.5 to 100 mg of a compound or mixture of compound of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or sacccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservativrs, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required. The following examples are illustrative of the invention and constitute especially preferred embodiments, The preferred diastereomers of these examples are isolated by column chromatography or fractional crystallization.

EXAMPLE 1

1-Carboxymethyl-3[(1-carboxy-3-phenylpropyl)amino]perhydroazocin-2-one

To a vigorously stirred suspension of 0.80 g. sodium hydride in 30 ml. tetrahydrofuran add over 20 min. a solution of 8.0 g. t-butyl iodoacetate and 5.86 g. 3,3-dichloroperhydroazocin-2-one [Nagasawa et al., J. Med. Chem. 14, 501 (1971)] dissolved in 60 ml. tetrahydrofuran. After the addition is completed, stir the reaction at room temperature for 1.5 hrs. then quench by the addition of 5 ml. of saturated $NH_4Cl$ solution. Filter the reaction and concentrate the filtrate. Add ether to the residue, filter and wash the filtrate with $H_2O$ and brine. Dry the ether solution and concentrate to obtain 9.3 g. 1-t-butoxycarbonylmethyl-3,3-dichloroperhydroazocin-2-one. Prepare an analytical sample by silica gel chromatography. M.p. 75–76.5. Anal. ($C_{13}H_{21}Cl_2NO_3$). Calc: C, 50.33; H, 6.82; N, 4.52. Found: C, 50.28; H, 7.05; N, 4.59.

To a solution of 3.10 g. of this ester in 20 ml. dioxane and 10 ml. $H_2O$ add 0.5 g. MgO and 0.3 g. 10% palladium on carbon. Hydrogenate this mixture under 40 psi hydrogen pressure at room temperature. Filter the reaction, concentrate the filtrate and add ether to the residue. Wash the ether with water and brine, dry and concentrate to 2.75 g. 1-t-butoxycarbonylmethyl-3-chloroperhydroazocin-2-one.

Prepare an analytical sample by silica gel chromatography using hexane:ethyl acetate. M.p. 97.5°–99°. Anal. ($C_{13}H_{22}ClNO_3$). Calc: C, 56.61; H, 8.04; N, 5.08; Cl, 12.85. Found: C, 56.79; H, 8.10; N, 5.06; Cl, 12.49.

Alternatively, react 4.12 g. 3-bromoperhydroazocin-2-one [Nagasawa et al., J. Med. Chem. 14, 501 (1971)] with 5.0 g. t-butyl iodoacetate and 0.55 g. sodium hydride as described above. Obtain after work up 5.10 g. 3-bromo-1-t-butoxycarbonylmethylperhydroazocin-2-one. Prepare an analytical sample by silica gel chromatography using hexane-ethyl acetate. M.P. 107.5–109. Anal. ($C_{13}H_{22}BrNO_3$). Calc: C, 48.75; H, 6.93; N, 4.37. Found: C, 48.78; H, 7.12; N, 4.26.

Prepare a solution of 15.6 g. of the monobromolactam in 500 ml. DMF. Add 2.43 g. NaI and 3.9 g. $NaN_3$ then heat the stirred mixture at 85°–90° for 16 hours. Concentrate the cooled reaction mixture in vacuo and partition the residue between 500 ml. ether and 100 ml. $H_2O$. Wash the ether layer with $H_2O$ and brine. Decolorize the ether solution with charcoal, dry and filter. Concentrate the filtrate to dryness. Add 25 ml. petroleum ether to the residue to precipitate 9.6 g. of 3-azido-1-t-butoxycarbonylmethylperhydroazocin-2-one.

Prepare an analytical sample by silica gel chromatography using hexaneethyl acetate. M.p. 101–102° C. Anal. ($C_{13}H_{22}N_4O_3$). Calc: C, 55.30; H, 7.85; N, 19.84. Found: C, 55.33; H, 8,07; N, 19.69.

Alternatively, the azidolactam can be prepared by this procedure from the monochlorolactam described above.

Dissolve 9.5 g. 3-azido-1-t-butoxycarbonylmethyl-perhydroazocin-2-one in 85 ml. ethanol. Hydrogenate at 40 psi hydrogen pressure at room temperature using 1.0 g. 10% palladium on charcoal as catalyst. Filter the reaction and concentrate the filtrate to obtain 3-amino-1-t-butoxycarbonylmethylperhydroazocin-2-one.

Secure an analytical sample by recrystallization from ether-hexane. M.p. 8788°. Anal. ($C_{13}H_{24}NO_3$). Calc: C, 60.90; H, 9.43; N, 10.93. Found: C, 60.99; H, 9.59; N, 10.71.

Hydrogenate a solution of 4.096 g. of this amine and 4.95 g. ethyl 2-oxo-4-phenyloxobutyrate in 150 ml. ethanol containing 0.96 g. acetic acid at 40 psi hydrogen pressure at room temperature using 0.5 g. 10% palladium on charcoal as catalyst. Filter the reaction mixture and concentrate the filtrate to dryness in vacuo. Chromatograph the residue on silica gel eluting with hexane-ethyl acetate. Isolate the desired racemic diastereomer (Isomer B) of 1-t-butoxycarbonylmethyl-3[(1-ethoxycarbonyl-3-phenylpropyl)amino]-1-perhydroazocin-2-one as the second one which elutes from the column. NMR ($CDCl_3$, TMS) $\delta$ 7.2 (s, 5H), $\delta$ 3.5–4.5 (m, 6H); $\delta$ 3.0–3.4 (m, 3H); $\delta$ 2.6–3.9 (m, 2H); $\delta$ 1.5–2.3 (m, ), $\delta$ 1.5 (s), $\delta$ 1.3 (t), total 22H. Anal. ($C_{25}H_{38}N_2O_5$). Calc: C, 67.24; H, 8.58; N, 6.27. Found: C, 66.96; H, 8.68; N, 6.06.

Isolate the minor racemic diastereomer (Isomer A) as the first one which elutes from the column.

Anal. ($C_{25}H_{38}N_2O_5$). Calc: C, 67.24; H, 8.58; N, 6.27 Found: C, 66.98; H, 8.69; N, 6.04.

Treat this diester (Isomer B) with trifluoroacetic acid. Concentrate the reaction mixture in vacuo and flush with $H_2O$ several times. Isolate 1-carboxymethyl-3-[(1-ethoxycarbonyl-3-phenylpropyl)amino]-1-perhydroazocin-2-one as the crystalline trifluoroacetate salt. M.p. 211°–213°. Anal. ($C_{21}H_{30}N_2O_5 \cdot CF_3CO_2H$). Calc: C, 54.11; H, 6.12; N, 5.49. Found: C, 54.12; H, 6.21; N, 5.82.

Remove the trifluoroacetic acid by passing the salt through a Dowex 50 ($H^+$) column and eluting with aqueous pyridine. NMR ($D_2O$, NaOD, TSS) $\delta$ 1.1 (t, 3H); $\delta$ 1.3–2.2 (m, 10H); $\delta$ 2.4–4.2 (m, 10H); $\delta$ 7.1 (s, 5H).

Treat the monoethyl ester trifluoroacetate salt (Isomer B) with 1M NaOH at room temperature. Pass the reaction mixture through a Dowex 50 ($H^+$) column eluting first with $H_2O$ then aqueous pyridine. Combine and concentrate the appropriate fractions and isolate 1-carboxymethyl-3-[(-1-carboxy-3-phenylpropyl)amino]perhydrozocin-2-one as a crystalline solid. m.p. 265–268(dec).

Anal. ($C_{19}H_{26}N_2O_5 \cdot 1/2 H_2O$) Calc.: C, 61.44; H, 7.26; N, 7.53. Found: C, 61.26; H, 7.38; N, 7.18.

Repeat the above sequence with Isomer A diester and isolate the Isomer A diacid.

EXAMPLE 2

1-Carboxymethyl-3-[(1-carboxy-4-phenylbutyl)amino]-perhydroazocin-2-one

React 2.56 g. 3-amino-1-t-butoxycarboxymethylperhydroazocin-2-one and 3.30 g. ethyl 5-phenyl-2-oxopentanoate with hydrogen using a palladium on carbon catalyst as described in Example 1. Work up the reaction as described above and isolate, after silica gel chromatography, two racemic diastereomeric diesters. Isomer A elutes first and Isomber B second.

Treat 900 mg. of Isomer B with 10 ml. trifluoroacetic acid at room temperature for 1.5 hr. Remove the trifluoroacetic acid in vacuo and obtain the monoethyl ester. Dissolve this ester in 10 ml 1M NaOH and store the solution at room temperature overnight. Chromatograph the reaction mixture on Dowex 50 ($H^+$) as described previously and isolate the diacid (Isomer B). M.p. 245-246.5 dec.

Treat Isomer A diester as described above and isolate the diacid as a freezedried white powder.

EXAMPLE 3

1-(1-Carboxyethyl)-3-[(1-carboxy-3-phenylpropyl)-amino]perhydroazocin-2-one

Prepare a solution of 250 mg. lithium azide in 6 ml. DMF and add to it 412 mg. 3-bromoperhydroazocin-2-one. Heat the reaction for 23 hrs. at 7075° under nitrogen, concentrate in vacuo, dissolve the residue in $H_2O$ and extract with ethyl acetate. Dry and concentrate the extracts to a semisolid residue. Chromatograph the crude product on silica gel eluting with 9:1 ethyl acetate: acetonitrile. Isolate 3-azidoperhydroazocin-2-one as a white solid (m.p. 108-109).

Add 156 mg. of this azide to a suspension of 30 mg. NaH in 3 ml. THF followed by a solution of 400 mg. methyl 2-iodopropionate in 2 ml. THF. Heat the reaction mixture under nitrogen at 55°-60° for 18 hours. After cooling, quench the reaction with $H_2O$. Add ether and wash the organic phase with 5% $NaHSO_3$, water and brine. Dry the organic phase and concentrate to an oil. Chromatograph this crude product on silica gel eluting with ethyl acetate hexane and isolate 3-azido-1-(1-carbomethoxyethyl)perhydroazocin-2-one. NMR ($DCCl_3$): δ 1.4-2.3 (d+m, 2H); δ 3.45 (m, 2H); δ 3.7 (s, 3H); δ 4.1(t, 1H); δ 4.6 (2xq, 1H).

Saponify this ester with dilute NaOH, acidify the reaction mixture and extract with methylene chloride. After drying and concentration of the extracts, isolate 3-azido-1-(1-carboxyethyl)-perhydroazocin-2-one. Fractionally crystallize this material from acetonitrile as the dicyclohexylamine salt to obtain the desired diastereomer.

Alternatively the diastereomers may be separated by reverse phase chromatography or elution from XAD-2 resin eluting with 8% $CH_3CN$-92% 0.05M pH 7 ammonium phosphate buffer. In either case, the desired isomer elutes first.

Convert this acid to its methyl ester using the method of Wang, J. Org. Chem., 42, 1286 (1977).

Convert this azide to the amine and react it with ethyl 2-oxo-4-phenylbutyrate as described in Example 1 to isolate, after silica gel chromatography, the diastereomers of 1-(1-methoxycarbonylethyl)-3-(1-ethoxycarbonyl-3-phenylpropyl)aminoperhydroazocin-2-one.

Isomer A—(elutes first): NMR ($CDCl_3$, TMS): δ 1.1-1.2 (d+t+m); δ 2.5-2.9 (m); δ 3.15 (t); 3.3 (broad s); δ 3.4-3.8 (m+s); δ 4.1 (q); δ 4.6 (q); δ 7.1 (s)

Anal. ($C_{23}H_{34}N_2O_5$). Calc.: C, 66.00; H, 8.18; N, 6.69. Found: C, 65.93; H, 8.43; N, 6.66.

Isomer B—(elutes second). NMR ($CDCl_3$, TMS): δ 1.0-2.2 (d+t+m); δ 2.5-2.9 (m); δ 3.15 (t); δ 3.45(s); δ 3.65 (s); δ 3.4-3.9 (broad) δ 4.1 (q); δ 4.4(q); δ 7.1 (s).

Anal ($C_{23}H_{34}N_2O_5$). Calc.: C, 66.00; H, 8.18; N, 6.69. Found: C, 65.63; H, 8.08; N, 6.53.

Hydrolyze each of these isomeric diesters with dilute sodium hydroxide. Chromatograph the hydrolysate over acid ion exchange resin and obtain, after lyophilization, the corresponding isomers of 1-(1-carboxyethyl)-3-(1-carboxy-3-phenylpropyl)aminoper hydroazocin-2-one.

Isomer A. Anal. ($C_{20}H_{28}N_2O_5$. $1\frac{1}{2}H_2O$). Calc.: C, 59,41; H, 7.73; N, 6.92. Found: C, 59,33; H, 7.42; N, 6.87.

Isomer B. Anal. ($C_{20}H_{28}N_2O_5.\frac{1}{4} H_2O$). Calc.: C, 63.05; H, 7.53; N, 7.35. Found: C, 63.13; H, 7.50; N, 7.28.

The other diastereomer of 3-azido-1-(carboxyethyl)-perhydroazocin-2-one also is converted to a second set of diastereomers of 1-(1-carboxyethyl)-3-(1-carboxy-3-phenylpropyl)aminoper hydroazocin-2-one as described above.

EXAMPLE 4

1-Carboxyethyl-3-[(1-carboxy-3-phenylpropyl)amino]per-hydroazocin-2-one

Reduce 3-azidoperhydroazocin-2-one (Example 3) to 3-aminoperhydroazocin-2-one using 10% Pd/C in ethanol. NMR ($CDCl_3$, TMS): δ 1.67 (broad s, 8H), δ 2.25 (broad s, 2H), δ 3.35 (m, 2H), δ 3.8 (m, 1H), δ 7.0 (broad, 1H). Hydrogenate a solution of 1.42 g of this amine, 0.59 g acetic acid and 3.09 g ethyl 2-oxo-4-phenylbutyrate in 50 ml ethanol over 10% Pd/C catalyst. AFter filtration and concentration of the reaction, purify the product by chromatography over silica gel to isolate 3-[(1-ethoxycarbonyl-3-phenyl-1-propyl)amino]perhydroazocin-2-one.

React this lactam with t-butyl rodoacetate in the presence of NaH as described in Example 1. Obtain, after chromatography over silica gel, isomers A and B of 1-t-butoxycarbonlymethyl-3-[(1-ethoxycarbonyl-3-phenylpropyl)amino]perhydroazocin-2-one as described in Example 1. Using the procedures described in Example 1, convert these diesters to the corresponding diacids.

EXAMPLE 5

1-Carboxymethyl-3-[(1-carboxy-3-phenylpropyl)amino]-8-methylperhydroazocin-2-one Cool a solution of 17 g 2-methylcycloheptanone in 75 ml concentrated hydrochloric acid and add protionwise 13.2 g sodium azide. Stir the reaction of 0° for 1 hour then at room temperature for 2 hours. Add the reaction to 150 ml ice water, bring to pH 7 with potassium carbonate and extract with chloroform. Treat the extracts with charcoal, dry over $MgSO_4$, filter and concentrate to obtain crude 8-methylperhydroazocin-2-one. Obtain a pure product by recrystallization from hexane (m.p. 70-73).

Anal. ($C_8H_{16}NO$). Calc.: C, 68.04; H, 10.71; N, 9.91. Found: C, 67.75; H, 10.74; N, 9.81.

Cool a solution of 16.9 ml $PBr_3$ in 70 ml benzene to 5° and add, with good stirring, 9.3 ml bromine dropwise. Then add a solution of 12.6 g of the lactam in 30 ml benzene. When the addition is completed, heat the reaction at 60° for 3 hours. Cool the reaction and add the lower layer to a mixture of $H_2O$ and $CH_2Cl_2$. After shaking, draw off the organic layer and extract the aqueous layer again. Wash the organic portions with $H_2O$ and 5% $NaHSO_3$. Dry over $Na_2SO_4$ and concentrate in vacuo to obtain 3-bromo-8-methylperhydroazocin-2-one. Purify the product by chromatography over silica gel.

Anal. ($C_8H_{15}BRNO$). Calc.: C, 43.65; H, 6.41; N, 6.36; Br, 36.31. Found: C, 43.84; H, 6.48; N, 6.28; Br, 36.14.

Dissolve 14.5 g of the bromolactam and 9.7 g lithium azide in 150 ml dimethylformamide and heat at 80°. Concentrate the reaction in vacuo and partition the residue between $H_2O$ and ethyl acetate. Dry the organic phase and concentrate to obtain 3-azido-8-methylperhydroazocin-2-one as a gummy solid. Trituration with ether gives a pure product (m.p. 111°–112°).

Anal. ($C_8H_{15}N_4O$). Calc.: C, 52.73; H, 7.74; N, 30.75. Found: C, 52.53; H, 7.82; N, 30.28.

React 5.65 g of this azide with 7.9 g t-butyl iodoacetate and 0.82 g sodium hydride as described in Example 1 to obtain 1-t-butoxycarbonylmethyl-3-azido-8-methylperhydroazocin-2-one, which can be purified by chromatography over silica gel. NMR ($CCl_4$, TMS): δ 1.0–2.2 (m); δ 1.3 (d); δ 1.45 (s); δ 3.45 (d, J=16h₃); δ 3.95 (d, J-16h₃); δ 4.3–5.1 (m).

Reduce 6.4 g of this azide to 1-t-butoxycarbonylmethyl-3-amino-8-methylperhydroazocin-2-one as described in Example 1. NMR ($CDCl_3$): δ 1.25 (d); δ 1.4 (s); δ 1.3–2.3 (m) δ 3.55 (d, J=16hz); δ 4.2 (d, J=16hz); δ 3.8–4.8 (m).

Hydrogenate 2.7 g of this amine with 3.9 g ethyl 2-oxo-4-phenylbutyrate and 0.59 g acetic acid as described in Example 1 to obtain 1-t-butoxycarbonylmethyl-3-[(1-ethoxycarbonyl-3-phenylpropyl)amino]-8-methylperhydroazocin-2-one as a mixture of diastereomers. Chromatograph this mixture over silica gel and obtain two racemic diastereomers.

Isomer A (elutes first). NMR ($CCl_4$, TMS): δ 1.2 (d); δ 1.3 (t); δ 1.45 (s); δ 1.3–2.2 (m); δ 2.4–2.8 )m); δ 3.3 (d, J-17hz); δ 3.2–3.4 (m); δ 3.7 (t); δ 4.1 (d, J=17hz); δ 4.1 (q); δ 7.1 (s).

Isomer B (elutes second). NMR ($CCl_4$, TMS): δ 1.15 (d); δ 1.25 (t); δ 1.45 (s); δ 1.1–2.2 (m); δ 2.5–2.9 (m); δ 3.25 (d, J=16hz); δ 3.2–3.65 (m); δ 4.0 (d, J=16hz); δ 4.1 (q); δ 7.1 (s).

Convert isomer B to 1-Carboxyethyl-3-(1-ethoxycarbonyl-3-phenylpropyl)amino-8-methylperhydroazocin-2-one trifluoroacetate salt as described in Example 1. NMR ($D_2O$-DCl, dioxane=3.63)=δ 1.1 (d); δ 1.2 (t) δ 1.4–2.2 (broad); δ 2.25 (m); δ 2.7 (m); δ 3.5 (broad); δ 3.7 (t); δ 4–4.5 (q+m); δ 7.15 (s).

Convert the above monoester to 1-carboxymethyl-3-(1-carboxy-3-phenylpropyl)amino-8-methylperhydroazocin-2-one as described in Example 1. NMR ($D_2O$+NaOD, dioxane=3.80): δ 1.3 (d); δ 1.8 (broad m) δ 2.7 (m); δ 3.2 (braod t); δ 3.55 (d, J=16h₃); δ 4.1 (d, J=16h₃); δ 3.6–4.2 (m); δ 7.35 (s).

EXAMPLE 6

(+)-1-Carboxymethyl-3-(S)-[(1-(S)-carboxy-3-phenyl propyl)amino]perhydroazocin-2-one Heat a mixture of 154.5 g 3-bromoperhydroazocin-2-one (Example 1), 58.6 g sodium azide, 215 ml ethanol and 215 ml $H_2O$ at 85°–90° for 22 hours. Store the solution at 0° for 2 hours and recover 98.4 g 3-azidoperhydroazocin-2-one. Isolate an additional 20.4 g from the mother liquors after concentration. Alkylate 100.6 g of this azide with 150.8 g t-butyl iodoacetate in the presence of 16.5 g sodium hydride as described in Example 1. Isolate 136.0 g 1-t-butoxycarbonylmethyl-3-azidoperhydroazocin-2-one. Reduce this azide to 1-t-butoxycarbonylmethyl-3-aminoperhydroazocin-2-one as described in Example 1.

Dissolve 94.7 g of this amine in 600 ml acetonitrile and add a warm (60°) solution of 47.5 g L-pyroglutamic acid in 2 l. acetonitrile. Stir the solution at room temperature for 2 hours then store at 4° for 18 hours. Filter and wash the solids with acetonitrile (2×200 ml) and isolate 56.4 g 1-t-butoxycarbonylmethyl-3-(R)-aminoperhydroazocin-2-one L-pyroglutamate. Purify this salt to constant melting point by repeated slurrying with acetonitrile (m.p. 183°–185°). Isolate (−)-1-t-butoxycarbonylmethyl-3-(R)-aminoperhydroazocin-2-one by treatment of the pure salt with aqueous ammonia, $[α]_{Na}^{25} = -43.3°$, (C=0.71, EtOH).

Concentrate the filtered mother liquors and dissolve the residue in 260 ml $H_2O$. Add 60 ml ammonium hydroxide and extract with ethyl acetate. Dry and concentrate the extracts to 61.1 g amine.

Dissolve this amine in 600 ml acetonitrile and add to 30.5 g D-pyroglutamic acid in 2 l. hot acetonitrile. Secure, after isolation and purification of the salt as described above, 51.6 g 1-t-butoxycarbonylmethyl-3-(S)-aminoperhydroazocin-2-one D-pyroglutamate (m.p. 183–185). Convert this salt to (+)-1-t-butoxycarbonylmethyl-3-(S)-aminoperhydroazocin-2-one as described above, $[α]_{Na}^{25}=43°$ (C=1.55, EtOH).

Hydrogenate this amine with ethyl 2-oxo-4-phenylbutyrate as described in Example 1 and isolate, after chromatography, (+)-1-t-butoxycarbonylmethyl-3-(S)-[(1-ethoxycarbonyl-3-phenylpropyl)amino]-perhydroazocin-2-one (Isomer B). Remove the t-butoxy ester with 4N HCl to obtain (+)-1-carboxymethyl-3-(S)-[(1-ethoxycarbonyl-3-phenylpropyl)amino]-perhydroazocin-2-one hydrochloride m.p. 171–173 (dec.).

Anal. ($C_{21}H_{30}N_2O_5$·HCl) Calc.: C. 59.08; H, 7.26; N, 6.56. Found: C, 58.79; H, 7.48; N, 6.57.

$[α]_{Na}^{25°} = 29.4°$ (C=1.8, EtOH).

Hydrolyze this monoester as described in Example 1 and isolate, after purification, (+)-1-carboxymethyl-3-(S)-[(1-carboxy-3-phenylpropyl)amino]-perhydroazocin-2-one.

Anal. ($C_{19}H_{26}N_2O_5$·1/4$H_2O$). Calc.: C, 62.21; H, 7.14; n, 7.72. Found: c, 62.09; H, 7.23; n, 7.63.

$[α]_{Na}^{25} = 47.2°$ (C=1.7, 1N NaOH).

EXAMPLE 7

(+)-1-Benzyloxycarbonylmethyl-3-(1-carboxy-3-phenylpropyl)aminoperhydroazocin-2-one (+)-3-Amino-1-t-butoxycarbonylmethylperhydroazocin-2-one (Example 6) is treated with HCl in ethyl acetate. After concentration, the residue is passed over an acid ion exchange resin and (+)-3-amino-1-carboxymethylperhydroazocin-2-one is eluted with 5% pyridine in water. $[α]_D^{25} = 93.9$ (C=1.80, $H_2O$).

A solution of 2.36 g of the hydrochloride salt of this amino acid in 15 ml benzyl alcohol is chilled to 0° and treated with 2 ml thionyl chloride. The mixture is kept 2 days at room temperature. The reaction is poured into ether and after stirring 30 minutes the ether is decanted from the gummy product. The ether solution is washed with water and the washings are used to dissolve the gum. The resulting aqueous solution is made basic and extracted with ethyl acetate. After drying and concentration (+)-3-amino-1-benzyloxycarbonylmethylperhydroazocin-2-one is isolated.

A solution of 929 mg of this benzyl ester, 3 g t-butyl 2-oxo-4-phenylbutyrate and 0.18 ml acetic acid in 10 ml ethanol is treated with 650 mg sodium cyanoborohydride in 30 ml ethanol over 3.5 hours. The reaction is then stirred at room temperature overnight. The reaction mixture is concentrated and the residue partitioned between ethyl acetate and 5% $NaHCO_3$. Concentration of the organic phase affords the crude product which is pruified by chromatography over silica gel (3:2 hexane:ethyl acetate) to give the isomers of 1-benzyloxycarbonylmethyl-3-(1-t-butoxycarbonyl-3-phenylpropyl)aminoperhydroazocin-2-one.

Isomer A (elutes first): $[\alpha]_D^{25} = -12.5°$ (C=2, EtOH).

Isomer B (elutes second): $[\alpha]_D^{25} = -4.2°$ (C=2, EtOH).

The t-butyl ester is removed from each isomer by treatment with HCl in ethyl acetate to afford 1-benzyloxycarbonylmethyl-3-(1-carboxy-3-phenylpropyl)-aminoperhydroazocin-2-one.

Isomer A: $[\alpha]_D^{25} = -27°$ (C=2, EtOH).
Isomer B: $[\alpha]_D^{25} = +17.5°$ (C=2, EtOH).

EXAMPLE 8

1-(1-Carboxyethyl)-3-(1-ethoxycarbonyl-3-phenylpropyl)aminoperhydroazocin-2-one.

Reduce the desired isomer of 3-azido-1-(1-carboxyethyl)perhydroazocin-2-one (Example 3) to 3-amino-1-(1-carboxyethyl)perhydroazocin-2-one with hydrogen and palladium on carbon as described in Example 7. Convert this amino acid to the benzyl ester hydrochloride.

React 1 mmole of this ester hydrochloride with 4 mmoles ethyl 2-oxo-4-phenylbutyrate, 1 mmole sodium acetate and 2-3 mmoles sodium cyanoborohydride in ethanol. Concentrate the reaction mixture and partition the residue between H$_2$O and ethyl acetate. Chromatograph the organic soluble portion over silica gel to isolate the diastereomers of 1-(1-benzyloxycarbonylethyl)-3-(1-carbethoxy-3-phenylpropyl)aminoperhydroazepin-2-one.

Hydrogenate each of the diastereomers over palladium on carbon in aqueous dioxane to obtain the respective diastereomers of 1-(1-carboxyethyl)-3-(1-carbethoxy-3-phenylpropyl)aminoperhydroazocin-2-one.

EXAMPLE 9

1-(1-Benzyloxycarbonylethyl)-3-(1-carboxy-3-phenylpropyl)aminoperhydroazocin-2-one The diastereomers of this compound may be prepared from 3-amino-1-(1-benzyloxycarbonylethyl)perhydroazocin-2-one (Example 8) and t-butyl 2-oxo-4-phenylbutyrate following the procudure in Example 7.

EXAMPLE 10

Monoester Products of Formula I with R$^2$ and R$^3$=H and R$^4$=OH

3-Amino-1-t-butoxycarbonylmethylperhydroazocin-2-one (Example 6) is reductively condensed with the α-ketoesters listed in Table I in place of ethyl 2-oxo-4-phenylbutyrate in the presence of palladium or carbon as described in Example 1. Work-up as described in that example including removal of the t-butyl ester affords the products of Formula I listed in Table II wherein R$^2$=R$^3$=H and R$^4$=OH.

Alternatively, the reductive condensation may be run in the presence of sodium cyanoborohydride as described in Example 7. After purification of the diesters and removal of the t-butyl ester, the compounds of Formula I as described above and listed in Table II are obtained.

EXAMPLE 11

Diacid Products of Formula I with R$^2$ and R$^3$=H and R=R$^4$=OH

Saponification of the products listed in Table II using the procedure described in Example 1 affords the products of Formula I listed in Table II wherein R$^2$, R$^3$=H and R, R$^4$=OH.

Alternatively, benzyl esters may be removed by catalytic hydrogenation in ethanol over 10% palladium on charcoal. Filtration and concentration of the reaction mixture will yield the products of Formula 1 described above.

EXAMPLE 12

Diacid Products of Formula I with R$^2$ and R$^3$=H and R and R$^4$=OH

3-Amino-1-t-butoxycarbonylmethylperhydroazocin-2-one is treated with 4N HCl in ethyl acetate to afford 3-amino-1-carboxymethylperhydroazocin-2-one hydrochloride. An aqueous solution of this hydrochloride and 3-5 equivalents of an α-ketoacid from Table III is adjusted to pH 6.5 with sodium hydroxide and treated with 3 equivalents of sodium cyanoborohydride for 18 hours. The product is absorbed on a strong acid ion exchange resin and eluted with 5% pyridine in water. Lyophilization affords the products of Formula I listed in Table II in which R$^2$, R$^3$=H and R, R$^4$=OH.

EXAMPLE 13

Diethyl Esters of Formula I with R$^2$ and R$^3$=H

Treatment of the diacids of Formula I listed in Table 2 (R$^2$, R$^3$=H and R, R$^4$=OH), which are prepared as described in Examples 9 or 10, with ethanol HCl affords the corresponding diester hydrochlorides of Formula 1 listed in Table II in which R$^2$, R$^3$=H and R, R$^4$=ethoxy. These hydrochlorides may be converted to the free base diesters by treatment with potassium carbonate and extraction with ethyl acetate. Drying and solvent removal affords the free bases.

EXAMPLE 14

Mono- and Diesters of Formula I where R$^2$ and R$^3$=H

Reaction of some of the α-ketoesters and α-ketoacids from Tables I and III with the benzyl or ethyl ester of 3-amino-1-carboxymethylperhydroazocin-2-one in the presence of sodium cyanoborohydride at neutral pH in a manner described in Examples 10 and 12 will afford the products listed in Table IV.

EXAMPLE 15

Monoester Products of Formula I where R$^2$ and H, R$^3$=CH$_3$ and R$^4$=OH

α-Ketoesters listed in Table I can be condensed with 3-amino-1-(1-benzyloxycarbonylethyl)perhydroazocin-2-one using the procudure described in Example 8 which, after purification, and hydrogenation as described, will afford the desired esters listed in Table II where R$^2$=H, R$^3$=CH$_3$ and R$^4$=OH.

Alternatively, when monobenzyl esters are desired, the condensation of 3-amino-1-(1-carboxyethyl)perhydroazocin-2-one with the required α-ketoesters in the presence of sodium cyanoborohydride may be used as described in Example 12.

EXAMPLE 16

Diacid Products of Formula I with R$^2$=H, R$^3$=CH$_3$ and R and R$^4$=OH

Saponification of the monoester products described in Example 15 using the procedure described in Example 1 affords the products of Formula I listed in Table II wherein R$^2$=H, R$^3$=CH$_3$ and R and R$^4$=OH.

EXAMPLE 17

Diacid Products of Formula I with $R^2=H$, $R^3=CH_3$ and R and $R^4=OH$

3-Amino-1-(1-carboxyethyl)azocin-2-one (Example 8) may be condensed with the α-ketoacids listed in Table III as described in Example 12 to afford the products listed in Table II wherein $R^2=H$, $R^3=CH_3$ and R and $R^4=OH$.

EXAMPLE 18

Diethyl Esters of Formula I with $R^2=H$, $R^3=CH_3$

Treatment of the diacids of Formula I listed in Table II ($R^2=H$, $R^3=CH_3$, $R=R^4=OH$) with ethanol-HCl as described in Example 13 affords the diesters listed in Table II wherein $R^2=H$, $R^3=CH_3$ and R and $R^4=OEt$.

EXAMPLE 19

Mono- and Diesters of Formula I where $R^2=H$ and $R^3=CH_3$

Readction of some of the α-ketoacids and α-ketoesters from Tables I and III with the benzyl or ethyl ester of 3-amino-1-(1-carboxyethyl)perhydroazocin-2-one in the presence of sodium cyanoborohydride in a manner dexcribed in Examples 10 and 12 would afford the products listed in Table IV wherein $R^2=H$ and $R^3=CH_3$.

EXAMPLE 20

Monoester Products of Formula I with $R^2=CH_3$ $R^3=H$ and $R^4=OH$

3-Amino-1-t-butoxycarbonylmethyl-8-methylperhydroazocin-2-one (Example 5) is reductively condensed with the α-ketoesters listed in Table I in the presence of palladium on carbon following the procedure described in Example 1. Product purification and t-butyl ester removal as described in this example will afford the products of Formula I listed in Table II wherein $R^2=CH_3$, $R^3=H$, and $R^4=OH$.

Alternatively, the reduction may be run in the presence of sodium cyanoborohydride as described in Example 7. After purification of the diester products and removal of the t-butyl ester the compounds of Formula I as described above will be obtained.

EXAMPLE 21

Diacid Products of Formula I with $R^2=CH_3$, $R^3=H$ and R and $R^4=OH$

The diacids of Formula I listed in Table II wherein $R^2=CH_3$, $R^3=H$ and R and $R^4=OH$ would be prepared from the esters ($R^2=CH^3$, $R^3=H$, R and $R^4=OH$) listed in Table II as described in Example 11.

EXAMPLE 22

Diacid Products of Formula I with $R^2=CH_3$, $R^3=H$, R and $R^4=OH$

3-Amino-1-carboxymethyl-8-methylperhydroazocin-2-one, prepared from the corresponding t-butyl ester (Example 5) as described in Example 12, may be condensed with the α-ketoacids listed in Table III as described in Example 12. Work-up and isolation would afford the compounds of Formula I listed Table II wherein $R^2=CH_3$, $R^3=H$, R and $R^4=OH$.

EXAMPLE 23

Diethyl Esters of Formula I with $R^2=CH_3$ and $R^3=H$

Treatment of the diacids of Formula I listed in Table II ($R^2=CH_3$, $R^3=H$, $R=R^4=OH$) with ethanol-HCl as described in Example 13 affords the diesters listed in Table II wherein $R^2=CH_3$, $R^3=H$, R and $R^4=OEt$.

EXAMPLE 24

Mono- and Diesters of Formula I with $R^2=CH_3$, $R^3=H$

Reaction of some of the α-ketoesters and α-ketoacids from Table I and III with the benzyl or ethyl ester of 3-amino-1-carboxymethyl-8-methylperhydroazocin-2-one in the presence of sodium cyanoborohydride in a manner described in Examples 10 and 12 would afford the products listed in Table IV wherein $R^2=CH_3$, $R^3=H$.

TABLE I

| | | α-Ketoesters |
|---|---|---|
| a. | Benzyl | 2-oxo-4-phenylbutyrate |
| b. | Ethyl | 4-p-chlorophenyl-2-oxobutyrate |
| c. | Ethyl | 4-(3-indolyl)-2-oxobutyrate |
| d. | Ethyl | 2-oxo-4-(2-thienyl)butyrate |
| e. | Ethyl | 2-oxo-4-(2-naphthyl)butyrate |
| f. | Ethyl | 4-p-hydroxyphenyl-2-oxobutyrate |
| g. | Ethyl | phenoxypyruvate |
| h. | Ethyl | 2-oxo-5-phenylpentanoate |
| i. | Ethyl | 4-p-methoxyphenyl-2-oxobutyrate |
| j. | Ethyl | 5-methyl-2-oxohexanoate |
| k. | Benzyl | 2-oxo-6-phthalimidohexanoate |

TABLE II

| | Products of Formula I | |
|---|---|---|
| | R | $R^1$ |
| l. | benzyloxy | phenethyl |
| m. | ethoxy | p-chlorophenethyl |
| n. | ethoxy | 3-indolylethyl |
| o. | ethoxy | 2-thienylethyl |
| p. | ethoxy | 2-naphthylethyl |
| q. | ethoxy | p-hydroxyphenethyl |
| r | ethoxy | phenoxymethyl |
| s. | ethoxy | 3-phenylpropyl |
| t. | ethoxy | p-methoxyphenethyl |
| u. | ethoxy | 3-methylbutyl |
| v. | benzyloxy | 4-phthalimidobutyl |
| w. | benzyloxy | 4-aminobutyl* |

*after hydrazinolysis of (v) under standard conditions

TABLE III

| | α-Ketoacids |
|---|---|
| x. | 2-oxo-4-phenylbutyric acid |
| y. | 4-p-chlorophenyl-2-oxobutyric acid |
| z. | 4-(3-indolyl)-2-oxobutyric acid |
| aa. | 2-oxo-4-(2-thienyl)butyric acid |
| bb. | 2-oxo-4-(2-naphthyl)butyric acid |
| cc. | 4-p-hydroxyphenyl-2-oxobutyric acid |
| dd. | phenoxypyruvic acid |
| ee. | 2-oxo-5-phenylpentanoic acid |
| ff. | 4-p-methoxyphenyl-2-oxohexanoic acid |
| gg. | 5-methyl-2-oxohexanoic acid |
| hh. | 2-oxo-6-phthalimidohexanoic acid |

TABLE IV

| Mono- and Diesters of Formula I with $R^2$ and $R^3 = H$ | | |
|---|---|---|
| R | $R^1$ | $R^4$ |
| ii. ethoxy | phenethyl | benzyloxy |
| jj. hydroxy | p-chlorophenethyl | benzyloxy |
| kk. hydroxy | 2-naphthylethyl | benzyloxy |

Alternatively benzyl esters may be cleaved catalytically as described in Example 11 to afford the products described above.

TABLE IV-continued

Mono- and Diesters of Formula I with $R^2$ and $R^3$ = H

| | R | $R^1$ | $R^4$ |
|---|---|---|---|
| ll. | hydroxy | 3-methylbutyl | benzyloxy |
| mm. | hydroxy | 4-aminobutyl | benzyloxy |
| nn. | hydroxy | phenethyl | ethoxy |
| oo. | benzyl | phenethyl | ethoxy |

EXAMPLE 25

$R^2$-Substituted Products of Formula I

The known 8-substituted enantholactams listed in Table V may be converted to 8-substituted-3-amino-1-t-butoxycarbonylmethylperhydroazocin-2-ones following the procedure described in Example 5 with the exception of 8-(2-aminoethyl)enantholactam which is carried through as the 8-(2-phthalimidylethyl)enantholactam.

Reaction of these aminolactams with ethyl 2-oxo-4-phenylbutyric acid and product purification as described in Example 5 will afford, after removal of the t-butyl ester, the products of Formula I listed in Table VI.

Dilute alkaline hydrolysis of the monoesters listed in Table VI (except the phthalimidyl derivative) followed by acidic ion exchange work-up would afford the diacids listed in Table VII.

TABLE V

8-Substituted Enantholactams

| | $R^2$ |
|---|---|
| pp. | Ethyl |
| qq. | n-Propyl |
| rr. | Cyclohexyl |
| ss. | 2-aminoethyl |

TABLE VI

Compounds of Formula I wherein R = OEt, $R^3$ = H and $R^4$ = OH

| | $R^1$ | $R^2$ |
|---|---|---|
| tt. | phenethyl | ethyl |
| uu. | phenethyl | n-propyl |
| vv. | phenethyl | cyclohexyl |
| ww. | phenethyl | 2-phthalimidylethyl |
| xx. | phenethyl | 2-aminoethyl* |

*after removal of the phthalimide moiety with hydrazine

TABLE VIII

Diacids of Formula I wherein $R^3$ = H, R and $R^4$ = OH.

| | $R^1$ | $R^2$ |
|---|---|---|
| yy. | phenethyl | ethyl |
| zz. | phenethyl | n-propyl |
| aaa. | phenethyl | cyclohexyl |
| bbb. | phenethyl | 2-aminoethyl |

EXAMPLE 26

Compressed Tablet containing 50 mg. of active ingredient

| | Per tablet, Mg. |
|---|---|
| 1-Carboxymethyl-3-[(1-carboxy-3-phenyl-1-propyl)amino]perhydroazocin-2-one | 5 |
| Calcium phosphate dibasic | 245 |
| Ethyl cellulose (as 5% solution in ethanol) | 5 |
| Unmixed granulation | 255 |

-continued

Compressed Tablet containing 50 mg. of active ingredient

| | Per tablet, Mg. |
|---|---|
| Add: | |
| Starch, corn | 14 |
| Magnesium stearate | 1 |
| | 270 |

EXAMPLE 27

| Dry filled capsule containing 5 mg. of active ingredient. | |
|---|---|
| | Per capsule, mg. |
| Lactose | 5 |
| Magnesium stearate | 273 |
| Mixed powders | 2 |
| | 280 |

Mix the active ingredient above, lactose, and magnesium stearate and reduce to a No. 60 mesh powder. Encapsulate, filling 280 mg. in each No. 2 capsule.

The above formulations can be employed to prepare compressed tablets or capsules of other novel compounds of this invention hereinbefore described.

The above examples describe the preparation of certain compounds which are illustrative of the novel compounds of this invention, and certain specific dosage forms suitable for administering the novel compounds, it is to be understood that the invention is not to be limited to the specific compounds described in the examples or by the specific reaction conditions described for the preparation of these compounds or by the specific ingredients included in the pharmaceutical preparations, but is to be understood to embrace variations and modifications thereof.

What is claimed is:

1. A compound of the formula:

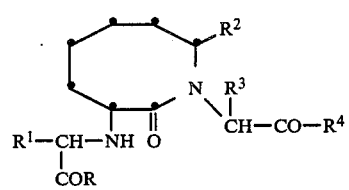

wherein
R and $R^4$ are the same or different and are
  hydroxy,
  lower alkoxy,
  lower alkenoxy,
  diloweralkylamino lower alkoxy,
  acetylaminoethoxy;
  nicotinoylaminoethoxy;
  succinimidoethoxy;
  pivaloyloxyethoxy;
  arloweralkoxy,
  amino,
  hydroxyamino;
$R^1$ is
  hydrogen,
  alkyl, alkenyl, and alkynyl of from 1 to 12 carbon atoms which include straight chain and branched groups;

cycloalkyl groups;
substituted loweralkyl wherein the substituent(s) can be halo, hydroxy, lower alkoxy or aryloxy, amino, loweralkylamino, aminoloweralkylthio, hydroxy, aminoloweralkoxy, diloweralkylamino, acetamido; benzamido; arylamino, guanidino, phthalimido, mercapto, loweralkylthio or arylthio, carboxy, carboxamido or carboloweralkoxy, arloweralkyl, arloweralkenyl, heteroarlower alkyl or heteroarlower alkenyl containing one heteroatom,
substituted arloweralkyl, or substituted heteroarlower alkyl containing one heteroatom, wherein the aryl or heteroaryl substituent(s) is halo, dihalo, lower alkyl, hydroxy, lower alkoxy, amino aminomethyl, phenyloxy, acetamido; benzamido; dilower alkylamino, loweralkylamino, carboxyl, haloloweralkyl;
substituted arloweralkyl or substituted heteroarloweralkyl containing one heteroatom, wherein the alkyl portion can be substituted by amino, hydroxy, acetamido or benzamido:

$R^3$ is hydrogen, lower alkyl, phenyl, phenyl lower alkyl, hydroxy phenyl lower alkyl, hydroxy lower alkyl, amino lower alkyl, acetamido or benzamido, lower alkyl, guanidino lower alkyl, imidazolyl lower alkyl, indolyl lower alkyl, mercapto lower alkyl or lower alkyl thio lower alkyl;

$R^2$ is hydrogen lower alkyl, cycloalkyl, aminoalkyl, hydroxyalkyl, aryl, substituted aryl, heteroaryl containing one heteroatom, aralkyl, heteroaralkyl containing one heteroatom, or substituted aryl wherein the substitutent is halo, alkyl, aminoalkyl, or alkoxy;
wherein in the foregoing $R$–$R_4$ groups inclusive:
the alkyl groups contain 2–12 carbon atoms; the loweralkyl groups contain 1–8 carbon atoms; the alkenyl and alkynyl grouPs contain 2–12 carbon atoms;
the loweralkenyl and loweralkynyl groups contain 2–8 carbon atoms;
aryl and the prefix "ar" denote unsubstituted aromatic rings of 6–12 carbon atoms;
the cycloalkyl groups are unsubstituted alkyl rings of 3–10 carbon atoms;
hetero denotes the heteroatoms N, O or S;
heteroaryl denotes an aryl group containing a heteroatom;
and, the pharmaceutically acceptable salts thereof.

2. A compound which is: 1-carboxymethyl-3-[(1-carboxy-3-phenylpropyl)amino]perhydroazocin-2-one.
3. A compound which is: 1-carboxymethyl-3-(S)-[(1(S)-carboxy-3-phenylpropyl) amino]perhydroazocin-2-one.
4. A compound which is: 1-benzyloxycarbonylmethyl-3-[(1-carboxy-3-phenylpropyl) amino]perhydroazocin-2-one.
5. A compound which is: 1-benzyloxycarbonylmethyl-3-(S)-[(1(S)-carboxy-3-phenylpropyl)amino]perhydroazocin-2-one.
6. A compound which is: 1-carboxymethyl-3-[(1-ethoxycarbonyl-3-phenylpropyl)amino]perhydroazocin-2-one.
7. A compound which is: 1-carboxymethyl-3(S)-[(1(S)-ethoxycarbonyl-3-phenylpropyl)amino]perhydroazocin-2-one.
8. A compouond which is: 1-carboxymethyl-3(S)-[(1(S)-ethoxycarbonyl-3-phenylpropyl)amino]perhydroazocin-2-one hydrochloride.
9. A compound which is: 1-ethoxycarbonylmethyl-3-[(1-ethoxycarbonyl-3-phenylpropyl)amino]perhydroazocin-2-one.
10. A compound which is: 1-ethoxycarbonylmethyl-3(S)-[(1(S)-ethoxycarbonyl-3-phenylpropyl)amino]perhydroazocin-2-one.
11. A compound which is: 1-(1-carboxyethyl)-3-[(1-ethoxycarbonyl-3-phenylpropyl)amino]perhydroazocin-2-one.
12. A compound which is: 1-carboxymethyl-3-[(1-ethoxycarbonyl-3-phenylpropyl) amino]-8-methylperhyroazocin-2-one.
13. A process for preparing compounds of the formula $$R^1-CH-NH \quad \underset{COR}{\overset{O}{\underset{\|}{N}}}\quad \overset{R^2}{\underset{CH-CO-R^4}{\overset{R^3}{|}}}$$

wherein
$R$ and $R^4$ are the same or different and are
hydroxy,
lower alkoxy,
lower alkenoxy,
aryloxy,
diloweralkylamino lower alkoxy,
acetylaminoethoxy,
nicotinoylaminoethoxy,
succinimidoethoxy,
and pivaloyloxyethoxy,
arloweralkoxy,
amino,
hydroxyamino;

$R^1$ is
hydrogen, alkyl, alkenyl, and alkynyl of from 1 to 12 carbon atoms which include straight chain and branched groups;
cycloalkyl groups;
substituted loweralkyl Wherein the substituent(s) can be halo, hydroxy, lower alkoxy or aryloxy, amino, loweralkylamino, aminoloweralkylthio, hydroxy. aminoloweralkoxy. diloweralkylamino, acetamido, benzamido, arylamino, guanidino, phthalimido, mercapto, loweralkylthio or arylthio, carboxy, carboxamido or carboloweralkoxy,
arloweralkyl, arloweralkenyl, heteroarlower alkyl containing one heteroatom or heteroarlower alkenyl containing one heteroatom,
substituted arloweralkyl or substituted heteroarlower alkyl containing one heteroatom, or substituted heteroarlower alkenyl containing one heteroatom, wherein the aryl or heteroaryl substituent(s) is halo, dihalo, lower alkyl, hydroxy, lower alkoxy, amino, aminomethyl, phenyloxy, acetamido, benzamido, diloweralkylamino, loweralkylamino, carboxyl, haloloweralkyl;
substituted arloweralkyl or substituted heteroarloweralkyl containing one heteroatom wherein the alkyl portion can be substituted by amino, hydroxy, acetamido, benzamido;

$R^3$ is hydrogen, lower alkyl, phenyl, phenyl lower alkyl, hydroxyphenyl lower alkyl, hydroxy lower alkyl, amino lower alkyl, acetamido or benzamido, lower alkyl, guanidino lower alkyl, imidazolyl lower alkyl, indolyl lower alkyl, mercapto lower alkyl or lower alkyl thio lower alkyl;

$R^2$ is hydrogen, lower alkyl, cycloalkyl, aminoalkyl, hydroxyalky, aryl, heteroaryl containing one heteroatom, aralkyl, heteroaralkyl containing one heteroatom, or substituted aryl wherein the substituent is halo, alkyl, aminoalkyl, or alkoxy; wherein in the foregoing $R-R_4$ groups inclusive:

the alkyl groups contain 2–12 carbon atoms: the loweralkyl groups contain 1–8 carbon atoms;

the alkenyl and alkynyl groups contain 2–12 carbon atoms;

the loweralkenyl and loweralkynyl groups contain 2–8 carbon atoms;

aryl and the prefix "ar" denote unsubstituted aromatic rings of 6–12 carbon atoms:

the cycloalkyl groups are unsubstituted alkyl rings of 3–10 carbon atoms;

hetero denotes the heteroatoms N, O or S;

heteroaryl denotes an aryl group containing a heteroatom;

which process comprises reductively alkylating a compound of the formula

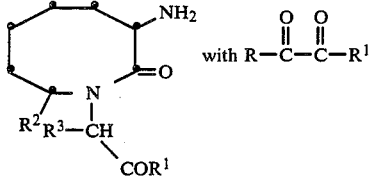

wherein R, $R^1$, $R^2$ and $R^3$ are as defined above, followed by removal of protecting groups, if necessary, to yield the desired product and, if desired, isolating the biologically more active isomer by chromatography, by fractional crystallization, or by resolution with an appropriate, optically active acid or base and, if further desired, preparing a salt of the desired product by conventional means.

* * * * *